United States Patent [19]
Bergsma et al.

[11] Patent Number: 5,955,308
[45] Date of Patent: Sep. 21, 1999

[54] CDNA CLONE HEAOD54 THAT ENCODES A HUMAN 7-TRANSMEMBRANE RECEPTOR

[75] Inventors: Derk J Bergsma, Berwyn; Wendy S Halsey, Kennett Square; Jeffrey L Mooney, Limerick; Ganesh M Sathe, King of Prussia, all of Pa.

[73] Assignee: SmithKline Beecham Corporation, Philadelphia, Pa.

[21] Appl. No.: 08/955,713

[22] Filed: Oct. 23, 1997

Related U.S. Application Data

[60] Provisional application No. 60/050,124, Jun. 18, 1997.

[51] Int. Cl.$^6$ ..................................................... C12N 15/12
[52] U.S. Cl. ........................ 435/69.1; 536/23.5; 536/24.3; 435/69.1; 435/252.3; 435/254.11; 435/320.1; 435/325
[58] Field of Search .................................. 536/23.5, 24.3; 435/69.1, 252.3, 254.11, 325, 320.1

[56] References Cited

PUBLICATIONS

Nomura, H. et al., "Molecular cloning of cDNs encoding a LD78 receptor and putative leukocyte chemotactic peptide receptors", Int. Immunol., vol. 5 (10), pp. 1239–1249, (1993).

Parr, C.E. et al., "Cloning and expression of a human $P_{2U}$ nucleotide receptor, a target for cyctic fibrosis pharmacotherapy", Proc. Natl. Acad. Sci. U.S.A., vol. 91, pp. 3275–3279, (1994).

*Primary Examiner*—Sally P. Teng
*Attorney, Agent, or Firm*—Elizabeth J. Hecht; Ratner & Prestia; William T. King

[57] ABSTRACT

HEOAD54 polypeptides and polynucleotides and methods for producing such polypeptides by recombinant techniques are disclosed. Also disclosed are methods for utilizing HEOAD54 polypeptides and polynucleotides in the design of protocols for the treatment of infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infraction; ulcers;astma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourettt's syndrome, among others, and diagnostic assays for such conditions.

13 Claims, No Drawings

CDNA CLONE HEAOD54 THAT ENCODES A HUMAN 7-TRANSMEMBRANE RECEPTOR

This application claims the benefit of U.S. Provisional Application No. 60/050,124, filed Jun. 18, 1997.

FIELD OF INVENTION

This invention relates to newly identified polynucleotides, polypeptides encoded by them and to the use of such polynucleotides and polypeptides, and to their production. More particularly, the polynucleotides and polypeptides of the present invention relate to the G-protein coupled receptor family, hereinafter referred to as HEOAD54. The invention also relates to inhibiting or activating the action of such polynucleotides and polypeptides.

BACKGROUND OF THE INVENTION

It is well established that many medically significant biological processes are mediated by proteins participating in signal transduction pathways that involve G-proteins and/or second messengers, in e.g., cAMP (Lefkowitz, Nature, 1991, 351:353–354). Herein these proteins are referred to as proteins participating in pathways with G-proteins or PPG proteins. Some examples of these proteins include the GPC receptors, such as those for adrenergic agents and dopamine (Kobilka, B. K., et al., Proc. Natl Acad. Sci., USA, 1987, 84:46–50; Kobilka, B. K., et al., Science, 1987, 238:650–656; Bunzow, J. R, et al., Nature, 1988, 336:783–787), G-proteins themselves, effector proteins, e.g., phospholipase C, adenyl cyclase, and phosphodiesterase, and actuator proteins, e.g., protein kinase A and protein kinase C (Simon, M. I., et al., Science, 1991, 252:802–8).

For example, in one form of signal transduction, the effect of hormone binding is activation of the enzyme, adenylate cyclase, inside the cell. Enzyme activation by hormones is dependent on the presence of the nucleotide, GTP. GTP also influences hormone binding. A G-protein connects the hormone receptor to adenylate cyclase. G-protein was shown to exchange GTP for bound GDP when activated by a hormone receptor. The GTP carrying form then binds to activated adenylate cyclase. Hydrolysis of GTP to GDP, catalyzed by the G-protein itself, returns the G-protein to its basal, inactive form. Thus, the G-protein serves a dual role, as an intermediate that relays the signal from receptor to effector, and as a clock that controls the duration of the signal.

The membrane protein gene superfamily of G-protein coupled receptors has been characterized as having seven putative transmembrane domains. The domains are believed to represent transmembrane α-helices connected by extracellular or cytoplasmic loops. G-protein coupled receptors include a wide range of biologically active receptors, such as hormone, viral, growth factor and neuroreceptors.

G-protein coupled receptors (otherwise known as 7TM receptors) have been characterized as including these seven conserved hydrophobic stretches of about 20 to 30 amino acids, connecting at least eight divergent hydrophilic loops. The G-protein family of coupled receptors includes dopamine receptors which bind to neuroleptic drugs used for treating psychotic and neurological disorders. Other examples of members of this family include, but are not limited to, calcitonin, adrenergic, endothelin, cAMP, adenosine, muscarinic, acetylcholine, serotonin, histamine, thrombin, kinin, follicle stimulating hormone, opsins, endothellal differentiation gene-1, rhodopsins, odorant, and cytomegalovirus receptors.

Most G-protein coupled receptors have single conserved cysteine residues in each of the first two extracellular loops which form disulfide bonds that are believed to stabilize functional protein structure. The 7 transmembrane regions are designated as TM 1, TM2, TM3, TM4, TM5, TM6, and TM7. TM3 has been implicated in signal transduction.

Phosphorylation and lipidation (palmitylation or farnesylation) of cysteine residues can influence signal transduction of some G-protein coupled receptors. Most G-protein coupled receptors contain potential phosphorylation sites within the third cytoplasmic loop and/or the carboxy terminus. For several G-protein coupled receptors, such as the β-adrenoreceptor, phosphorylation by protein kinase A and/or specific receptor kinases mediates receptor desensitization.

For some receptors, the ligand binding sites of G-protein coupled receptors are believed to comprise hydrophilic sockets formed by several G-protein coupled receptor transmembrane domains, said sockets being surrounded by hydrophobic residues of the G-protein coupled receptors. The hydrophilic side of each G-protein coupled receptor transmembrane helix is postulated to face inward and form a polar ligand binding site. TM3 has been implicated in several G-protein coupled receptors as having a ligand binding site, such as the TM3 aspartate residue. TM5 serines, a TM6 asparagine and TM6 or TM7 phenylalanines or tyrosines are also implicated in ligand binding.

G-protein coupled receptors can be intracellularly coupled by heterotrimeric G-proteins to various intracellular enzymes, ion channels and transporters (see, Johnson et al., Endoc. Rev., 1989, 10:317–331) Different G-protein α-subunits preferentially stimulate particular effectors to modulate various biological functions in a cell. Phosphorylation of cytoplasmic residues of G-protein coupled receptors have been identified as an important mechanism for the regulation of G-protein coupling of some G-protein coupled receptors. G-protein coupled receptors are found in numerous sites within a mammalian host.

Over the past 15 years, nearly 350 therapeutic agents targeting 7 trarsmembrane (7 TM) receptors have been successfully introduced into the market.

This indicates that these receptors have an established, proven history as therapeutic targets. Clearly there is a need for identification and characterization of further receptors which can play a role in preventing, ameliorating or correcting dysfunctions or diseases, including, but not limited to, infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome.

SUMMARY OF THE INVENTION

In one aspect, the invention relates to HEOAD54 polypeptides and recombinant materials and methods for their production. Another aspect of the invention relates to methods for using such HEOAD54 polypeptides and polynucleotides. Such uses include the treatment of infections such as bacterial, fungal, protozoan and viral infections, particularly infections caused by HIV-1 or HIV-2; pain; cancers; anorexia; bulimia; asthma; Parkinson's disease;

acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, among others. In still another aspect, the invention relates to methods to identify agonists and antagonists using the materials provided by the invention, and treating conditions associated with HEOAD54 imbalance with the identified compounds. Yet another aspect of the invention relates to diagnostic assays for detecting diseases associated with inappropriate HEOAD54 activity or levels.

DESCRIPTION OF THE INVENTION
Definitions

The following definitions are provided to facilitate understanding of certain terms used frequently herein.

"HEOAD54" refers, among others, to a polypeptide comprising the amino acid sequence set forth in SEQ ID NO:2, or an allelic variant thereof.

"Receptor Activity" or "Biological Activity of the Receptor" refers to the metabolic or physiologic function of said HEOAD54 including similar activities or improved activities or these activities with decreased undesirable side-effects. Also included are antigenic and immunogenic activities of said HEOAD54.

"HEOAD54 gene" refers to a polynucleotide comprising the nucleotide sequence set forth in SEQ ID NO: 1 or allelic variants thereof and/or their complements.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Tolypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-inking, cyclization, disulfide bond formation, demethylation, formation of covalent cross-inks, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation,racemization, selenoylation, sulfation, transfer-RNA mediated addition of amino acids to proteins such as arginylation, and ubiquitination. See, for instance, PROTEINS - STRUCTURE AND MOLECULAR PROPERTIES, 2nd Ed., T. E. Creighton, W. H. Freeman and Company, New York, 1993 and Wold, F., Posttranslational Protein Modifications: Perspectives and Prospects, pgs. 1–12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", *Meth Enzymol* (1990) 182:626–646 and Rattan et aL, "Protein Synthesis: Posttranslational Modifications and Aging", *Ann NY Acad Sci* (1992) 663:48–62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity" is a measure of the identity of nucleotide sequences or amino acid sequences. In general, the sequences are aligned so that the highest order match is obtained. "Identity" per se has an art-recognized meaning and can be calculated using published techniques. See, e.g.: (COMPUTATIONAL MOLECULAR BIOLOGY, Lesk, A. M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds., Humana Press, New Jersey, 1994; SEQUENCE ANALYSIS IN MOLECULAR BIOLOGY, von Heinje, G., Academic Press, 1987; and SEQUENCE ANALYSIS PRIMER, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H., and Lipton, D., *SIAM J Applied Math* (1988) 48:1073). Methods commonly employed to determine identity or similarity between two sequences include, but are not limited to, those disclosed in Guide to Huge Computers, Martin J. Bishop, ed., Academic Press, San Diego, 1994, and Carillo, H., and Lipton, D., *SIAM J Applied Math* (1988) 48:1073. Methods to determine identity and similarity are codified in computer programs. Preferred computer program methods to determine identity and similarity between two sequences include, but are not limited to, GCS program package (Devereux, J., et al., *Nucleic Acids Research* (1984) 12(1):387), BLASTP, BLASTN, FASTA (Atschul, S.F. et al., *J Molec Biol* (1990) 215:403).

As an illustration, by a polynucleotide having a nucleotide sequence having at least, for example, 95% "identity" to a reference nucleotide sequence of SEQ ID NO: 1 is intended that the nucleotide sequence of the polynucleotide is identical to the reference sequence except that the polynucleotide sequence may include up to five point mutations per each 100 nucleotides of the reference nucleotide sequence of SEQ ID NO: 1. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5 or 3 terminal positions of the reference nucleotide sequence or anywhere between those terminal positions, interspersed either individually among nucleotides in the reference sequence or in one or more contiguous groups within the reference sequence.

Similarly, by a polypeptide having an amino acid sequence having at least, for example, 95% "identity" to a reference amino acid sequence of SEQ ID NO:2 is intended that the amino acid sequence of the polypeptide is identical to the reference sequence except that the polypeptide sequence may include up to five amino acid alterations per each 100 amino acids of the reference amino acid of SEQ ID NO: 2. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

Polypeptides of the Invention

In one aspect, the present invention relates to HEOAD54 polypeptides (or HEOAD54 proteins). The HEOAD54 polypeptides include the polypeptides of SEQ ID NOS:2 and 4; as well as polypeptides comprising the amino acid sequence of SEQ ID NO:2; and polypeptides comprising the amino acid sequence which have at least 80% identity to that of SEQ ID NO:2 over its entire length, and still more preferably at least 90% identity, and even still more preferably at least 95% identity to SEQ ID NO: 2. Furthermore, those with at least 97–99% are highly preferred. Also included within HEOAD54 polypeptides are polypeptides having the amino acid sequence which have at least 80% identity to the polypeptide having the amino acid sequence of SEQ ID NO: 2 over its entire length, and still more preferably at least 90% identity, and even still more preferably at least 95% identity to SEQ ID NO: 2. Furthermore, those with at least 97–99% are highly preferred. Preferably, HEOAD54 polypeptides exhibit at least one biological activity of the receptor.

The HEOAD54 polypeptides may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

Fragments of the HEOAD54 polypeptides are also included in the invention. A fragment is a polypeptide having an amino acid sequence that entirely is the same as par; but not all, of the amino acid sequence of the aforementioned HEOAD54 polypeptides. As with HEOAD54 polypeptides, fragments may be "free-standing," or comprised within a larger polypeptide of which they form a part or region, most preferably a s a single continuous region. Representative examples of polypeptide fragments of the invention, include, for example, fragments from about amino acid number 1–20, 21–40, 41–60, 61–80, 81–100, and 101 to the end of HEOAD54 polypeptide. In this context "about" includes the particularly recited ranges larger or smaller by several, 5, 4, 3, 2 or 1 amino acid at either extreme or at both extremes.

Preferred fragments include, for example, truncation polypeptides having the amino acid sequence of HEOAD54 polypeptides, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Other preferred fragments are biologically active fragments. Biologically active fragments are those that mediate receptor activity, including those with a similar activity or an improved activity, or with a decreased undesirable activity. Also included are those that are antigenic or immunogenic in an animal, especially in a human.

Preferably, all of these polypeptide fragments retain the biological activity of the receptor, including antigenic activity. Among the most preferred fragment is that having the amino acid sequence of SEQ ID NO: 4. Variants of the defined sequence and fragments also form part of the present invention. Preferred variants are those that vary from the referents by conservative amino acid substitutions—i.e., those that substitute a residue with another of like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, or 1–2 amino acids are substituted, deleted, or added in any combination.

The HEOAD54 polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

Polynucleotides of the Invention

Another aspect of the invention relates to HEOAD54 polynucleotides. HEOAD54 polynucleotides include isolated polynucleotides which encode the HEOAD54 polypeptides and fragments, and polynucleotides closely related thereto. More specifically, HEOAD54 polynucleotides of the invention include a polynucleotide comprising the nucleotide sequence contained in SEQ ID NO: 1 encoding an HEOAD54 polypeptide of SEQ ID NO: 2, and polynucleotides having the particular sequences of SEQ ID NOS:1 and 3. HEOAD54 polynucleotides further include a polynucleotide comprising a nucleotide sequence that has at least 80% identity over its entire length to a nucleotide sequence encoding the HEOAD54 polypeptide of SEQ ID NO:2, and a polynucleotide comprising a nucleotide sequence that is at least 80% identical to that of SEQ ID NO: 1 over its entire length. In this regard, polynucleotides at least 90% identical are particularly preferred, and those with at least 95% are especially preferred. Furthermore, those with at least 97% are highly preferred and those with at least 98–99% are most highly preferred, with at least 99% being the most preferred. Also included under HEOAD54 polynucleotides are a nucleotide sequence which has sufficient identity to a nucleotide sequence contained in SEQ ID NO: 1 to hybridize under conditions useable for amplification or for use as a probe or marker. The invention also provides polynucleotides which are complementary to such HEOAD54 polynucleotides.

HEOAD54 of the invention is structurally related to other proteins of the G-protein coupled receptor family, as shown by the results of sequencing the cDNA encoding human HEOAD54. The cDNA sequence of SEQ ID NO:1 contains an open reading frame (nucleotide number 236 to 1504) encoding a polypeptide of 423 amino acids of SEQ ID NO:2. The amino acid sequence of Table 1 (SEQ ID NO:2) has about 40.2% identity (using FASTA) in 291 amino acid residues with human probable G-protein coupled receptor, HM74 (Accession # P49019, Nomura, H. et al, Int. Immunol. 5: 1239–1249, 1993). Furthermore, HEOAD54 (SEQ ID NO: 2) is 27.3% identical to human P2U purinoceptor over 341 amino acid residues (Accession # P41231, Parr, C. E. et al, Proc. Natl. Sci. U.S.A. 91: 3275–3279, 1994). The nucleotide sequence of Table 1 (SEQ ID NO: 1) has about 98.25 % identity (using BLAST) in 171 nucleotide residues with yc63g05.r1 Homo sapiens cDNA clone 85400 5' (Accession # T72122, Wilson, R et al, WashU-Merck EST project, Unpublished, 1995). Furthermore, HEOAD54 (SEQ ID NO:1) is 55.59% identical to human G-protein coupled receptor mRNA over 349 nucleic acid residues (Accession # U35398, An,S. et al, Unpublished, 1995). Thus, HEOAD54 polypeptides and polynucleotides of the present invention are expected to have, inter alia, similar biological functions/ properties to their homologous polypeptides and polynucleotides, and therutility is obvious to anyone skilled in the art.

TABLE 1<sup>a</sup>

| 1 | GACTATCCTC | CCACTTCAGG | GTTTCTCTGG | GCTTCCATCT | TGCCCCTGCT |
|---|---|---|---|---|---|
| 51 | GAGCCCTGCT | TCCTCCTCTA | CCAGCAGCAC | AACCCCCAGG | CTGGGCTCAG |
| 101 | AGACCTCATG | TGGTGGGATC | ACTCAGTACC | CCGAGGCGGA | GGGAAGGAGG |
| 151 | GAGGGCTGCA | GGGTTCCCCT | TGGCCTGCAA | ACAGGAACAC | AGGGTGTTTC |
| 201 | TCAGTGGCTG | CGAGAATGCT | GATGAAAACC | CCAGGATGTT | GTGTCACCGT |
| 251 | GGTGGCCAGC | TGATAGTGCC | AATCATCCCA | CTTTGCCCTG | AGCACTCCTG |
| 301 | CAGGGGTAGA | AGACTCCAGA | ACCTTCTCTC | AGGCCCATGG | CCCAAGCAGC |
| 351 | CCATGGAACT | TCATAACCTG | AGCTCTCCAT | CTCCCTCTCT | CTCCTCCTCT |
| 401 | GTTCTCCCTC | CCTCCTTCTC | TCCCTCACCC | TCCTCTGCTC | CCTCTGCCTT |
| 451 | TACCACTGTG | GGGGGGTCCT | CTGGAGGGCC | CTGCCACCCC | ACCTCTTCCT |
| 501 | CGCTGGTGTC | TGCCTTCCTG | GCACCAATCC | TGGCCCTGGA | GTTTGTCCTG |
| 551 | GGCCTGGTGG | GGAACAGTTT | GGCCCTCTTC | ATCTTCTGCA | TCCACACGCG |
| 601 | GCCCTGGACC | TCCAACACGG | TGTTCCTGGT | CAGCCTGGTG | GCCGCTGACT |
| 651 | TCCTCCTGAT | GAGCAACCTG | CCCCTCCGCG | TGGACTACTA | CCTCCTCCAT |

TABLE 1a-continued

| | | | | |
|---|---|---|---|---|
| 701 | GAGACCTGGC | GCTTTGGGGC | TGCTGCCTGC | AAAGTCAACC | TCTTCATGCT |
| 751 | GTCCACCAAC | CGCACGGCCA | GCGTTGTCTT | CCTCACAGCC | ATCGCACTCA |
| 801 | ACCGCTACCT | GAAGGTGGTG | CAGCCCCACC | ACGTGCTGAG | CCGTGCTTCC |
| 851 | GTGGGGGCAG | CTGCCCGGGT | GGCCGGGGGA | CTCTGGGTGG | GCATCCTGCT |
| 901 | CCTCAACGGG | CACCTGCTCC | TGAGCACCTT | CTCCGGCCCC | TCCTGCCTCA |
| 951 | GCTACAGGGT | GGGCACGAAG | CCCTCGGCCT | CGCTCCGCTG | GCACCAGGCA |
| 1001 | CTGTACCTGC | TGGAGTTCTT | CCTGCCACTG | GCGCTCATCC | TCTTTGCTAT |
| 1051 | TGTGAGCATT | GGGCTCACCA | TCCGGAACCG | TGGTCTGGGC | GGGCAGGCAG |
| 1101 | GCCCGCAGAG | GGCCATGCGT | GTGCTGGCCA | TGGTGGTGGC | CGTCTACACC |
| 1151 | ATCTGCTTCT | TGCCCAGCAT | GATCTTTGGC | ATGGCTTCCA | TGGTGGCTTT |
| 1201 | CTGGCTGTCC | GCCTGCCGCT | CCCTGGACCT | CTGCACACAG | CTCTTCCATG |
| 1251 | GCTCCCTGGC | CTTCACCTAC | CTCAACAGTG | TCCTGGACCC | CGTGCTCTAC |
| 1301 | TGCTTCTCTA | GCCCCAACTT | CCTCCACCAG | AGCCGGGCCT | TGCTGGGCCT |
| 1351 | CACGCGGGGC | CGGCAGGGCC | CAGTGAGCGA | CGAGAGCTCC | TACCAACCCT |
| 1401 | CCAGGCAGTG | GCGCTACCGG | GAGGCCTCTA | GGAAGGCGGA | GGCCATAGGG |
| 1451 | AAGCTGAAAG | TGCAGGGCGA | GGTCTCTCTG | GAAAAGGAAG | GCTCCTCCCA |
| 1501 | GGGCTGAGGG | CCAGCTGCAG | GGCTGCAGCG | CTGTGGGGGT | AAGGGCTGCC |
| 1551 | GCGCTCTGGC | CTGGAGGGAC | AAGGCCAGCA | CACGGTGCCT | CAAC | aA nucleotide sequence of a human HEOAD54 (SEQ ID NO: 1).

TABLE 2b

| | | | | |
|---|---|---|---|---|
| 1 | MLCHRGGQLI | VPIIPLCPEH | SCRGRRLQNL | LSGPWPKQPM | ELHNLSSPSP |
| 51 | SLSSSVLPPS | PSPSPSSAPS | APTTVGGSSG | GPCHPTSSSL | VSAFLAPILA |
| 101 | LEFVLGLVGN | SLALFIPCIN | TRPWTSNTVF | LVSLVAADFL | LISNLPLRVD |
| 151 | YYLLHETWRP | GAAACKVNLF | MLSTNRTASV | VFLTAIALNR | YLKVVQPHHV |
| 201 | LSRASVGAAA | RVAGGLWVGI | LLLNGHLLLS | TFSGPSCLSY | RVGTKPSASL |
| 251 | RWHQALYLLE | FFLPLALILF | AIVSIGLTIR | NRGLGGQAGP | QRAMRVLAMV |
| 301 | VAVYTICFLP | SIIPGMASMV | AFWLSACRSL | DLCTQLFHGS | LAFRYLNSVL |
| 351 | DPVLYCPSSP | NFLHQSRALL | GLTRGRQGPV | SDESSYQPSR | QWRYREASRK |
| 401 | AEAIGKLKVQ | GEVSLEKEGS | SQG | | | bAn amino acid sequence of a human HEOAD54 (SEQ ID NO: 2).

One polynucleotide of the present invention encoding HEOAD54 may be obtained using standard cloning and screening, from a cDNA library derived from mRNA in cells of human Eosinophils using the expressed sequence tag (EST) analysis (Adams, M. D., et al. *Science* (1991) 252:1651–1656; Adams, M. D. et al., *Nature*, (1992) 355:632–634; Adams, M. D., et al., *Nature* (1995) 377 Supp:3–174). Polynucleotides of the invention can also be obtained from natural sources such as genomic DNA libraries or can be synthesized using well known and commercially available techniques.

The nucleotide sequence encoding the HEOAD54 polypeptide of SEQ ID NO:2 may be identical to the polypeptide encoding sequence contained in Table, 1 (nucleotide number 236 to 1504 of SEQ ID NO:1), or it may be a sequence, which as a result of the redundancy (degeneracy) of the genetic code, also encodes the polypeptide of SEQ ID NO:2.

When the polynucleotides of the invention are used for the recombinant production of the HEOAD54 polypeptide, the polynucleotide may include the coding sequence for the mature polypeptide or a fragment thereof, by itself, the coding sequence for the mature polypeptide or fragment in reading frame with other coding sequences, such as those encoding a leader or secretory sequence, a pre-, or pro- or prepro- protein sequence, or other fusion peptide portions.

For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., Proc Natl Acad Sci USA (1989) 86:821–824, or is an HA tag. The polynucleotide may also contain noncoding 5' and 3' sequences, such as transcribed, non-translated sequences, splicing and polyadenylation signals, ribosome binding sites and sequences that stabilize mRNA.

Further preferred embodiments are polynucleotides encoding HEOAD54 variants comprising the amino acid sequence of the HEOAD54 polypeptide of Table 2 (SEQ ID NO:2) in which several, 5–10, 1–5, 1–3, 1–2 or 1 amino acid residues are substituted, deleted or added, in any combination. Among the preferred polynucleotides of the present invention is contained in Table 3 (SEQ ID NO: 3) encoding the amino acid sequence of Table 4 (SEQ ID NO: 4).

TABLE 3[c]

GGCACGAGCTGCCTTCCTGGCACCAATCCTGGCCCTGGAGTTTGTCCTGGGCCTGGTGGGAACAGTTT
GGCCCTCTTCATCTTCTGCATCCACACGCGGCCCTGGACCTCCAACACGGTGTTCCTGGTCAGCCTGGT
GGCCGCTGACTTCCTCCTGATCAGCAACCTGCCCCTCCGCGTGGACTACTACCTCCTCCATGAGACCTG
GCGCTTTGGGGCTGCTGCCTGCAAAGTCAACCTCTTCATGCTGTCNACCAACCGCAAGGCCAGCGTTGT
CTTCCTCACAGCCATCGCACTCAACCGCTACCTGAAGGTGGTGCANCCCCACCACGTGCTGAACCGTGC
TTCCGTGGGGCANCTGCCCGGGTGGNCGGGGAATCTGGGTGGGCATCCTGCTCCTCAACGGGNACCT
GCTCCTGAACACCTTCTCCGGCCCCTCCTGCCTCAGCTACAGGGTGGGCACGAARCCCTCGGCCTCGCT
CCGCTGGCACCAGGCACTGTACCTGCTGGARTTYTTCCTGCCACTGGCGCTCATCCTCTTTGCTATTGT
GAGCATTGGGCTCACCATCCGGAACCGTGGTCTGGGCGGGCAGGCAGGCCCGCAGAGGGCCATGCGTGT
NCTGGCCATGGTGGTGGCYGTCTACACCATCTGCTTCTTGCCCAGCATCATCTTTGGCATGGCTTCCAT
GGTGGCTTTCTGGCTGTCCGCCTGCCGATCCCTGGACCTCTGCACACAGCTCTTCCATGGCTCCCTGGC
CTTCACCTACCTCAACAGTGTCCTGGACCCCGTGCTCTACTGCTTCTCTAGCCCCAACTTCCTCCACCA
GAACCGGGCCTTGCTGGGCCTCACGCGGGGCCGGCAGGGCCCAGTGAGCGACGAAAGCTCCTACCAACC
CTCCAGGCAGTGGCGCTACCGGGAGGCCTCTAGGAAGGCGGARGCCATAGGGAAGCTGAAAGTGCAGGG
CGAGGTCTCTCTGGAAAAGGAAGGCTCCTCCCAAGGGCTGAAGGCCAGCTGCAGGGCTGCAGCGCTGTG
GGGGTAAGGGCTGCCGCGCTCTGGCCTGGARGGACAAGGCCAGCACACGGTGCCTCAACCAACTGGACA
AGGGATGGCGGCAGACCARGGGCCAGGCCAAAGCACTGGCAGGACTCAGGTGGGTGGCAGGKARARAAA
CCCACCTTAGGCCTCTCAGTGTGTCCAGGATGGCATTCCCAGAATGCAGGGGAGAGCAGGATGCCGGGT
GGAGGAGACAGGCAAGGTGCCGTTGGCACACCAGCTCAGACAGGGGCCTGCGCAGCTGCAGGGGACAGA
CGCCCAATCACTGTCACAGCAGAGTCACCTTAGAAATTGGACAGCTGCATGTTCTGTGCTCTCCAGTTT
GTCCCTTCCAATATTAATAAACTTCCCTTTTAAATATAAAAAAAAAAAAAAAAAA

[c]A partial nucleotide sequence of a human HEOAD54 (SEQ ID NO: 3).

TABLE[d]

ARAAFLAPILALEFVLGLVGNSLALFIFCIHTRPWTSNTVFLVSLVAADFLLISNLPLRVDYYLLHETW
RFGAAACKVNLFMLSTNRKASVVFLTAIALNRYLKVVXPHHVLNRASVGAXARVXGGIWVGILLLNGXL
LLNTFSGPSCLSYRVGTKPSASLRWHQALYLLEFFLPLALILFAIVSIGLTIRNRGLGGQAGPQRAMRV
LAMVVAVYTICFLPSIIFGMASMVAFWLSACRSLDLCTQLFHGSLAFTYLNSVLDPVLYCFSSPNFLHQ
NRALLGLTRGRQGPVSDESSYQPSRQWRYREASRKAEAIGKLKVQGEVSLEKEGSSQGLKASCRAAALW
G.GLPRSGLEGQGQHTVPQPTGQGMAADQGPGQSTGRTQVGGRXXNPP.ASQCVQDGIPRMQGRAGCRV
EETGKVPLAHQLRQGPAQLQGTDAQSLSQQSHLRNWTAACSVLSSLSLPILINFPFKYKKKKKK

[d]A partial amino acid sequence of a human HEOAD54 (SEQ ID NO: 4).

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 80%, and preferably at least 90%, and more preferably at least 95%, yet even more preferably 97–99% identity between the sequences.

Polynucleotides of the invention, which are identical or sufficiently identical to a nucleotide sequence contained in SEQ ID NO: 1 or a fragment thereof, may be used as hybridization probes for cDNA and genomic DNA, to isolate full-length cDNAs and genomic clones encoding HEOAD54 and to isolate cDNA and genomic clones of other genes (including genes encoding homologs and orthologs from species other than human) that have a high sequence similarity to the HEOAD54 gene. Such hybridization techniques are known to those of skill in the art. Typically these nucleotide sequences are 80% identical, preferably 90% identical, more preferably 95% identical to that of the referent. The probes generally will comprise at least 15 nucleotides. Preferably, such probes will have at least 30 nucleotides and may have at least 50 nucleotides. Particularly preferred probes will range between 30 and 50 nucleotides.

One embodiment, to obtain a polynucleotide encoding the HEOAD54 polypeptide, including homologs and orthologs from species other than human, comprises the steps of screening an appropriate library under stringent hybridization conditions with a labeled probe having the SEQ ID NO: 1 or a fragment thereof (including that of SEQ ID NO: 3), and isolating fill-length cDNA and genomic clones containing said polynuclotide sequence. Such hybridization techniques are well known to those of skill in the art. Stringent hybridization conditions are as defined above or alternatively conditions under overnight incubation at 42° C. in a solution comprising: 50% formamide, 5×SSC (150 mM NaCl, 15mM trisodium citrate), 50 mM sodium phosphate (pH7.6), 5× Denhardtes solution, 10% dextran sulfate, and 20 microgram/ml denatured, sheared salmon sperm DNA, followed by washing the filters in 0.1×SSC at about 65° C.

The polynucleotides and polypeptides of the present invention may be employed as research reagents and materials for discovery of treatments and diagnostics to animal and human disease.

Vectors, Host Cells, Expression

The present invention also relates to vectors which comprise a polynucleotide or polynucleotides of the present invention, and host cells which are genetically engineered with vectors of the invention and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., *BASIC METHODS IN MOLECULAR BIOLOGY* (1986) and Sambrook et al., *MOLECULAR CLONING: A LABORATORY MANUAL,* 2nd Ed., Cold Spring Harbor Laboratory Press, Cold Spring Harbor, N.Y. (1989) such as calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as streptococci, staphylococci, *E. coli, Streptomyces* and *Bacillus subtilis* cells; fingal cells, such as yeast cells and *Aspergillus* cells; insect cells such as *Drosophila* S2 and *Spodoptera Sf9* cells; animal cells such as CHO, COS, HeLa, C127, 3T3, BHK, HEK 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., *MOLECULAR CLONING, A LABORATORY MANUAL* (supra).

For secretion of the translated protein into the lumen of the endoplasmic reticulum, into the periplasmic space or into the extracellular environment, appropriate secretion signals may be incorporated into the desired polypeptide. These signals may be endogenous to the polypeptide or they may be heterologous signals.

If the HEOAD54 polypeptide is to be expressed for use in screening assays, generally, it is preferred that the polypeptide be produced at the surface of the cell. In this event, the cells may be harvested prior to use in the screening assay. If the HEOAD54 polypeptide is secreted into the medium, the medium can be recovered in order to recover and purify the polypeptide; if produced intracellularly, the cells must first be lysed before the polypeptide is recovered.

HEOAD54 polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

Diagnostic Assays

This invention also relates to the use of HEOAD54 polynucleotides for use as diagnostic reagents. Detection of a mutated form of the HEOAD54 gene associated with a dysfunction will provide a diagnostic tool that can add to or define a diagnosis of a disease or susceptibility to a disease which results from under-expression, over-expression or altered expression of HEOAD54. Individuals carrying mutations in the HEOAD54 gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzrtically by using PCR or other amplification techniques prior to analysis. RNA or cDNA may also be used in similar fashion. Deletions and insertions can be dect by a change in size of the amplified product in comparison to the normal genotype. Point mutations can be identified by hybridizing amplified DNA to labeled HEOAD54 nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing. See, eg., Myers et al, *Science* (1985)230:1242. Sequence changes at specific locations may also be revealed by nuclease protection assays, such as RNase and S1protection or the chemical cleavage method. See Cotton et al., *Proc Natl Acad Sci USA* (1985) 85: 4397–4401. In another embodiment, an array of oligonucleotides probes comprising the HEOAD54 nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability. (See for example: M.Chee et al., Science, Vol 274, pp 610–613 (1996)).

The diagnostic assays offer a process for diagnosing or determining a susceptibility to infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome through detection of mutation in the HEOAD54 gene by the methods described.

In addition, infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, can be diagnosed by methods comprising determining from a sample derived from a subject an abnormally decreased or increased level of the HEOAD54 polypeptide or HEOAD54 mRNA. Decreased or increased expression can be measured at the RNA level using any of the methods well known in the art for the quantitation of polynucleotides, such as, for example, PCR, RT-PCR, RNase protection, Northern blotting and other hybridization methods. Assay techniques that can be used to determine levels of a protein, such as an HEOAD54, in a sample derived from a host are well-known to those of skill in the art. Such assay methods include radioimmunoassays, competitive-binding assays, Western Blot analysis and ELISA assays.

Thus in another aspect, the present invention relates to a diagnostic kit for a disease or suspectability to a disease, particularly infections such as bacterial, fungal, protozoan and viral 3infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy, and psychotic and neurological disorders, including anxiety, schizophrenia, manic depression, delirium, dementia, severe mental retardation and dyskinesias, such as Huntington's disease or Gilles dela Tourett's syndrome, which comprises:

(a) an HEOAD54 polynucleotide, preferably the nucleotide sequence of SEQ ID NO: 1, or a fragment thereof;

(b) a nucleotide sequence complementary to that of (a);

(c) an HEOAD54 polypeptide, preferably the polypeptide of SEQ ID NO: 2, or a fragment thereof, or (d) an antibody to an HEOAD54 polypeptide, preferably to the polypeptide of SEQ ID NO: 2. It will be appreciated that in any such kit, (a), (b), (c) or (d) may comprise a substantial component.

Chromosome Assays

The nucleotide sequences of the present invention are also valuable for chromosome identification. The sequence is specifically targeted to and can hybridize with a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found, for example, in V. McKusick, Mendelian heritance in Man (available on line through Johns Hopkins University Welch Medical Library). The relationship between genes and diseases that have been mapped to the same chromosomal region are then identified through linkage analysis (coinheritance of physically adjacent genes).

The differences in the cDNA or genomic sequence between affected and unaffected individuals can also be determined. If a mutation is observed in some or all of the affected individuals but not in any normal individuals, then the mutation is likely to be the causative agent of the disease.

Antibodies

The polypeptides of the invention or their fragments or analogs thereof or cells expressing them can also be used as immunogens to produce antibodies inmmunospecific for the HEOAD54 polypeptides. The term "immunospecific" means that the antibodies have substantially greater affinity for the polypeptides of the invention than their affinity for other related polypeptides in the prior art.

Antibodies generated against the HEOAD54 polypeptides can be obtained by administering the polypeptides or epitope-bearing fragments, analogs or cells to an animal, preferably a nonhuman, using routine protocols. For preparation of monoclonal antibodies, any technique which provides antibodies produced by continuous cell line cultures can be used. Examples include the hybridoma technique (Kohler, G. and Milstein, C., *Nature* (1975)256:495–497), the trioma technique, the human B-cel hybridoma technique (Kozbor et al., *Immunology Today* (1983) 4:72) and the EBV-hybridoma technique (Cole et al., MONOCLONAL ANTIBODIES AND CANCER THERAPY, pp. 77–96, Alan R. Liss, Inc., 1985).

Techniques for the production of single chain antibodies (U.S. Pat. No. 4,946,778) can also be adapted to produce single chain antibodies to polypeptides of this invention. Also, transgenic mice, or other organisms including other mammals, may be used to express humanized antibodies.

The above-described antibodies may be employed to isolate or to identify clones expressing the polypeptide or to purify the polypeptides by affinity chromatography.

Antibodies against HEOAD54 polypeptides may also be employed to treat infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, among others.

Vaccines

Another aspect of the invention relates to a method for inducing an immunological response in a mammal which comprises inoculating the mammal with the HEOAD54 polypeptide, or a fragment thereof, adequate to produce antibody and/or T cell immune response to protect said animal from infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome, among others. Yet another aspect of the invention relates to a method of inducing immunological response in a mammal which comprises delivering an HEOAD54 polypeptide via a vector directing expression of an HEOAD54 polynucleotide in vivo in order to induce such an immunological response to produce antibody to protect said animal from diseases.

Further aspect of the invention relates to an immunological/vaccine formulation (composition) which, when introduced into a mammalian host, induces an immunological response in that mammal to an HEOAD54 polypeptide wherein the composition comprises an HEOAD54 polypeptide or HEOAD54 gene. The vaccine formulation may further comprise a suitable carrier. Since the HEOAD54 polypeptide may be broken down in the stomach, it is preferably administered parenterally (including subcutaneous, intramuscular, intravenous, intradermal etc. injection). Formulations suitable for parenteral administration include aqueous and non-aqueous sterile injection solutions which may contain anti-oxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Screening Assays

The HEOAD54 polypeptide of the present invention may be employed in a screening process for compounds which bind the receptor and which activate (agonists) or inhibit activation of (antagonists) the receptor polypeptide of the present invention. Thus, polypeptides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics. See Coligan et al., Current Protocols in Immunology 1(2): Chapter 5 (1991).

HEOAD54 polypeptides are responsible for many biological functions, including many pathologies. Accordingly, it is desirous to find compounds and drugs which stimulate HEOAD54 on the one hand and which can inhibit the function of HEOAD54 on the other hand. In general, agonists are employed for therapeutic and prophylactic purposes for such conditions as infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome. Antagonists may be employed for a variety of therapeutic and prophylactic purposes for such conditions as infections such as bacterial, fungal, protozoan and viral infections, particularly infections caused by HIV-1 or HIV-2; pain; cancers; anorexia; bulimia; asthma, Parkinson's disease; acute heart failure; hypotension; hypertension; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome.

In general, such screening procedures involve producing appropriate cells which express the receptor polypeptide of the present invention on the surface thereof Such cells include cells from animals, yeast, Drosophila or E. coli. Cells expressing the receptor (or cell membrane containing the expressed receptor) are then contacted with a test compound to observe binding, or stimulation or inhibition of a functional response.

One screening technique includes the use of cells which express the receptor of this invention (for example, transfected CHO cells) in a system which measures extracellular pH or intracellular calcium changes caused by receptor activation. In this technique, compounds may be contacted with cells expressing the receptor polypeptide of the present invention. A second messenger response, e.g., signal transduction, pH changes, or changes in calcium level, is then measured to determine whether the potential compound activates or inhibits the receptor.

Another method involves screening for receptor inhibitors by determining inhibition or stimulation of receptor-mediated cAMP and/or adenylate cyclase accumulation. Such a method involves transfecting a eukaryotic cell with the receptor of this invention to express the receptor on the cell surface. The cell is then exposed to potential antagonists in the presence of the receptor of this invention. The amount of cAMP accumulation is then measured. If the potential antagonist binds the receptor, and thus inhibits receptor binding, the levels of receptor-mediated cAMP, or adenylate cyclase, activity will be reduced or increased.

Another method for detecting agonists or antagonists for the receptor of the present invention is the yeast based technology as described in U.S. Pat. No. 5,482,835, incorporated by reference herein.

The assays may simply test binding of a candidate compound wherein adherence to the cells bearing the receptor is detected by means of a label directly or indirectly associated with the candidate compound or in an assay involving competition with a labeled competitor. Further, these assays may test whether the candidate compound results in a signal generated by activation of the receptor, using detection systems appropriate to the cells bearing the receptor at their surfaces. Inhibitors of activation are generally assayed in the presence of a known agonist and the effect on activation by the agonist by the presence of the candidate compound is observed.

Further, the assays may simply comprise the steps of mixing a candidate compound with a solution containing a HEOAD54 polypeptide to form a mixture, measuring HEOAD54 activity in the mixture, and comparing the HEOAD54 activity of the mixture to a standard.

The HEOAD54 cDNA, protein and antibodies to the protein may also be used to configure assays for detecting the effect of added compounds on the production of HEOAD54 mRNA and protein in cells. For example, an ELISA may be constructed for measuring secreted or cell associated levels of HEOAD54 protein using monoclonal and polyclonal antibodies by standard methods known in the art, and this can be used to discover agents which may inhibit or enhance the production of HEOAD54 (also called antagonist or agonist, respectively) from suitably manipulated cells or tissues. Standard methods for conducting screening assays are well understood in the art.

Examples of potential HEOAD54 antagonists include antibodies or, in some cases, oligonucleotides or proteins which are closely related to the ligand of the HEOAD54, e.g., a fragment of the ligand, or small molecules which bind to the receptor but do not elicit a response, so that the activity of the receptor is prevented.

Thus in another aspect, the present invention relates to a screening kit for identifying agonists, antagonists, ligands, receptors, substrates, enzymes, etc. for HEOAD54 polypeptides; or compounds which decrease or enhance the production of HEOAD54 polypeptides, which comprises:

(a) an HEOAD54 polypeptide, preferably that of SEQ ID NO:2;

(b) a recombinant cell expressing an HEOAD54 polypeptide, preferably that of SEQ ID NO:2;

(c) a cell membrane expressing an HEOAD54 polypeptide; preferably that of SEQ ID NO: 2; or (d) antibody to an HEOAD54 polypeptide, preferably that of SEQ ID NO: 2.

It will be appreciated that in any such kit, (a), (b), (c) or (d) may comprise a substantial component.

Prophylactic and Therapeutic Methods

This invention provides methods of treating an abnormal conditions related to both an excess of and insufficient amounts of HEOAD54 activity.

If the activity of HEOAD54 is in excess, several approaches are available. One approach comprises administering to a subject an inhibitor compound (antagonist) as hereinabove described along with a pharmaceutically acceptable carrier in an amount effective to inhibit activation by blocking binding of ligands to the HEOAD54, or by inhibiting a second signal, and thereby alleviating the abnormal condition.

In another approach, soluble forms of HEOAD54 polypeptides still capable of binding the ligand in competition with endogenous HEOAD54 may be administered. Typical embodiments of such competitors comprise fragments of the HEOAD54 polypeptide.

In still another approach, expression of the gene encoding endogenous HEOAD54 can be inhibited using expression blocking techniques. Known such techniques involve the use of antisense sequences, either internally generated or separately administered. See, for example, O'Connor, *J Neurochem* (1991) 56:560 in *Oligodeoxvnucleotides as Antisense Inhibitors of Gene Expression*, CRC Press, Boca Raton, Fla. (1988). Alternatively, oligonucleotides which form triple helices with the gene can be supplied. See, for example, Lee et al., *Nucleic Acids Res* (1979) 6:3073; Cooney et al., *Science* (1988) 241:456; Dervan et al., *Science* (1991) 251:1360. These oligomers can be administered per se or the relevant oligomers can be expressed in vivo.

For treating abnormal conditions related to an underexpression of HEOAD54 and its activity, several approaches are also available. One approach comprises administering to a subject a therapeutically effective amount of a compound which activates HEOAD54, i.e., an agonist as described above, in combination with a pharmaceutically acceptable carrier, to thereby alleviate the abnormal condition. Alternatively, gene therapy may be employed to effect the endogenous production of HEOAD54 by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For overview of gene therapy, see Chapter 20, *Gene Therapy and other Molecular Genetic-based Therapeutic Approaches*, (and references cited therein) in Human Molecular Genetics, T Strachan and A P Read, BIOS Scientific Publishers Ltd (1996).

Formulation and Administration

Peptides, such as the soluble form of HEOAD54 polypeptides, and agonists and antagonist peptides or small molecules, may be formulated in combination with a suitable pharmaceutical carrier. Such formulations comprise a therapeutically effective amount of the polypeptide or compound, and a pharmaceutically acceptable carrier or excipient. Such carriers include but are not limited to, saline, buffered saline, dextrose, water, glycerol, ethanol, and combinations thereof. Formulation should suit the mode of administration, and is well within the skill of the art. The invention further relates to pharmaceutical packs and kits comprising one or more containers filled with one or more of the ingredients of the aforementioned compositions of the invention.

Polypeptides and other compounds of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible.

Administration of these compounds may also be topical and/or localize, in the form of salves, pastes, gels and the like.

The dosage range required depends on the choice of peptide, the route of administration, the nature of the formulation, the nature of the subject's condition, and the judgment of the attending practitioner. Suitable dosages, however, are in the range of 0.1–100 μg/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

EXAMPLE 1

Mammlian Cell Expression

The receptors of the present invention are expressed in either human embryonic kidney 293 (HEK293) cells or adherent dhfr CHO cells. To maximize receptor expression, typically all 5' and 3' untranslated regions (UTRs) are removed from the receptor cDNA prior to insertion into a pCDN or pCDNA3 vector. The cells are transfected with individual receptor cDNAs by lipofectin and selected in the presence of 400 mg/ml G418. After 3 weeks of selection, individual clones are picked and expanded for further analysis. HEK293 or CHO cells transfected with the vector alone serve as negative controls. To isolate cell lines stably expressing the individual receptors, about 24 clones are typically selected and analyzed by Northern blot analysis. Receptor mRNAs are generally detectable in about 50% of the G418-resistant clones analyzed.

EXAMPLE 2

Ligand bank for binding and functional assays.

A bank of over 200 putative receptor ligands has been assembled for screening. The bank comprises: transmitters, hormones and chernokines known to act via a human seven transmenbrane (7T1M) receptor; naturally occurring compounds which may be putative agonists for a human 7TM receptor, non-mammalian, biologically active peptides for which a mammalian counterpart has not yet been identified; and compounds not found in nature, but which activate 7TM receptors with unknown natural ligands. This bank is used to initially screen the receptor for known ligands, using both functional (i.e. calcium, cAMP, microphysiometer, oocyte electrophysiology, etc, see below) as well as binding assays.

EXAMPLE 3

Ligand Binding Assays

Ligand binding assays provide a direct method for ascertaig receptor pharmacology and are adaptable to a high throughput format. The purified ligand for a receptor is radiolabeled to high specific activity (50–2000 Ci/mmol) for binding studies. A determination is then made that the process of radiolabeling does not diminish the activity of the ligand towards its receptor. Assay conditions for buffers, ions, pH and other modulators such as nucleotides are optimized to establish a workable signal to noise ratio for both membrane and whole cell receptor sources. For these assays, specific receptor binding is defined as total associated radioactivity minus the radioactivity measured in the presence of an excess of unlabeled competing ligand. Where possible, more than one competing ligand is used to define residual nonspecific binding.

EXAMPLE 4

Functional Assay in Xenopus Oocytes

Capped RNA transcripts from linearized plasmid templates encoding the receptor cDNAs of the invention are synthesized in vitro with RNA polymerases in accordance with standard procedures. In vitro transcripts are suspended in water at a final concentration of 0.2 mg/ml. Ovarian lobes are removed from adult female toads, Stage V defolliculated oocytes are obtained, and RNA transcripts (10 ng/oocyte) are injected in a 50 nl bolus using a microinjection apparatus. Two electrode voltage clamps are used to measure the currents from individual Xenopus oocytes in response to agonist exposure. Recordings are made in Ca2+ free Barth's medium at room temperature. The Xenopus system can be used to screen known ligands and tissue/cell extracts for activating ligands.

EXAMPLE 5

Microphysiometric Assays

Activation of a wide variety of secondary messenger systems results in extrusion of small amounts of acid from a cell. The acid formed is largely as a result of the increased metabolic activity required to fuel the intracellular signaling process. The pH changes in the media surrounding the cell are very small but are deteable by the CYTOSENSOR microphysiometer (Molecular Devices Ltd., Menlo Park, Calif.). The CYTOSENSOR is thus capable of detecting the activation of a receptor which is coupled to an energy utilizing intracellular signaling pathway such as the G-protein coupled receptor of the present invention.

EXAMPLE 6

Extract/Cell Supematant Screening

A large number of mammalian receptors exist for which there remains, as yet, no cognate activating ligand (agonist). Thus, active ligands for these receptors may not be included within the ligands banks as identified to date. Accordingly, the 7TM receptor of the invention is also functionally screened (using calcium, cAMP, microphysiometer, ooyte electrophysiology, etc., functional screens) against tissue extracts to identify natural ligands. Extracts that produce positive functional responses can be sequentially subfractionated until an activating ligand is isolated and identified.

EXAMPLE 7

Calcium and cAMP Functional Assays

7TM receptors which are expressed in HEK 293 cells have been shown to be coupled functionally to activation of PLC and calcium mobilization and/or cAMP stimuation or inhibition. Basal calcium levels in the HEK 293 cells in receptor-transfected or vector control cells were observed to be in the normal, 100 nM to 200 nM, range. HEK 293 cells expressing recombinant receptors are loaded with fura 2 and in a single day more than 150 selected ligands or tissue/cell extracts are evaluated for agonist induced calcium mobilization. Similarly, HEK 293 cells expressing recombinant receptors are evaluated for the stimulation or inhibition of cAMP production using standard cAMP quantitation assays.

Agonists presenting a calcium transient or cAMP fluctuation are tested in vector control cells to determine if the response is unique to the transfected cells expressing receptor.

All publications, including but not limited to patents and patent applications, cited in this specification are herein incorporated by reference as if each individual publication were specifically and individually indicated to be incorporated by reference herein as though fully set forth.

What is claimed is:

1. An isolated polynucleotide comprising a nucleotide sequence encoding the polypeptide comprising the amino acid sequence set forth in SEQ ID NO:2.

2. The isolated polynucleotide of claim 1 wherein said polynucleotide comprises nucleotides 236 to 1504 of the nucleotide sequence set forth in SEQ ID NO: 1.

3. The isolated polynucleotide of claim 1, wherein said polynucleotide consists of the entire nucleotide sequence set forth in SEQ ID NO: 1.

4. The isolated polynucleotide of claim 1 comprising an RNA sequence corresponding to the entire length of the nucleotide sequence set forth in SEQ ID NO: 1.

5. The isolated polynucleotide of claim 1 comprising an RNA sequence corresponding to nucleotides 236 to 1504 of the nucleotide sequence set forth in SEQ ID NO: 1.

6. An isolated expression vector comprising a polynucleotide expressing a polypeptide comprising the amino acid sequence set forth in SEQ ID NO:2.

7. A host cell comprising the expression vector of claim 6.

8. A process for producing a polypeptide comprising the amino acid sequence set forth in SEQ ID NO:2 comprising culturing the host cell of claim 7 under conditions sufficient for the production of said polypeptide and recovering said polypeptide from the culture.

9. A isolated membrane of the host cell of claim 7 expressing a polypeptide comprising the amino acid sequence set forth in SEQ ID NO:2.

10. A process for producing a cell which produces a polypeptide comprising the amino acid sequence set forth in SEQ ID NO:2 comprising transforming or transfecting a host cell with the expression vector of claim 6 such that the host cell, under appropriate culture conditions, produces said polypeptide.

11. A host cell produced by the process of claim 10, expressing a polypeptide comprising the amino acid sequence set forth in SEQ ID NO:2.

12. An isolated polynucleotide comprising a nucleotide sequence containing up to a total of 5 alterations per each 100 nucleotides of a nucleotide sequence encoding the amino acid sequence set forth in SEQ ID NO:2, said alterations being selected from the group consisting of deletions, additions, and substitutions.

13. An isolated polynucleotide which is complementary to any of the isolated polynucleotides in any one of claims 1, 2, 3, 6, 4, 5, and 12.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 1594 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
GACTATCCTC CCACTTCAGG GTTTCTCTGG GCTTCCATCT TGCCCCTGCT GAGCCCTGCT      60

TCCTCCTCTA CCAGCAGCAC AACCCCCAGG CTGGGCTCAG AGACCTCATG TGGTGGGATC     120

ACTCAGTACC CCGAGGCGGA GGGAAGGAGG GAGGGCTGCA GGGTTCCCCT TGGCCTGCAA     180

ACAGGAACAC AGGGTGTTTC TCAGTGGCTG CGAGAATGCT GATGAAAACC CCAGGATGTT     240

GTGTCACCGT GGTGGCCAGC TGATAGTGCC AATCATCCCA CTTTGCCCTG AGCACTCCTG     300

CAGGGGTAGA AGACTCCAGA ACCTTCTCTC AGGCCCATGG CCCAAGCAGC CCATGGAACT     360

TCATAACCTG AGCTCTCCAT CTCCCTCTCT CTCCTCCTCT GTTCTCCCTC CCTCCTTCTC     420

TCCCTCACCC TCCTCTGCTC CCTCTGCCTT TACCACTGTG GGGGGGTCCT CTGGAGGGCC     480

CTGCCACCCC ACCTCTTCCT CGCTGGTGTC TGCCTTCCTG GCACCAATCC TGGCCCTGGA     540

GTTTGTCCTG GGCCTGGTGG GGAACAGTTT GGCCCTCTTC ATCTTCTGCA TCCACACGCG     600

GCCCTGGACC TCCAACACGG TGTTCCTGGT CAGCCTGGTG GCCGCTGACT TCCTCCTGAT     660

CAGCAACCTG CCCCTCCGCG TGGACTACTA CCTCCTCCAT GAGACCTGGC GCTTTGGGGC     720

TGCTGCCTGC AAAGTCAACC TCTTCATGCT GTCCACCAAC CGCACGGCCA GCGTTGTCTT     780

CCTCACAGCC ATCGCACTCA ACCGCTACCT GAAGGTGGTG CAGCCCCACC ACGTGCTGAG     840

CCGTGCTTCC GTGGGGGCAG CTGCCCGGGT GGCCGGGGGA CTCTGGGTGG GCATCCTGCT     900

CCTCAACGGG CACCTGCTCC TGAGCACCTT CTCCGGCCCC TCCTGCCTCA GCTACAGGGT     960

GGGCACGAAG CCCTCGGCCT CGCTCCGCTG GCACCAGGCA CTGTACCTGC TGGAGTTCTT    1020

CCTGCCACTG GCGCTCATCC TCTTTGCTAT TGTGAGCATT GGGCTCACCA TCCGGAACCG    1080

TGGTCTGGGC GGGCAGGCAG GCCCGCAGAG GGCCATGCGT GTGCTGGCCA TGGTGGTGGC    1140

CGTCTACACC ATCTGCTTCT TGCCCAGCAT CATCTTTGGC ATGGCTTCCA TGGTGGCTTT    1200

CTGGCTGTCC GCCTGCCGCT CCCTGGACCT CTGCACACAG CTCTTCCATG GCTCCCTGGC    1260

CTTCACCTAC CTCAACAGTG TCCTGGACCC CGTGCTCTAC TGCTTCTCTA GCCCCAACTT    1320

CCTCCACCAG AGCCGGGCCT TGCTGGGCCT CACGCGGGGC CGGCAGGGCC CAGTGAGCGA    1380

CGAGAGCTCC TACCAACCCT CCAGGCAGTG GCGCTACCGG GAGGCCTCTA GGAAGGCGGA    1440
```

```
GGCCATAGGG AAGCTGAAAG TGCAGGGCGA GGTCTCTCTG GAAAAGGAAG GCTCCTCCCA      1500

GGGCTGAGGG CCAGCTGCAG GGCTGCAGCG CTGTGGGGGT AAGGGCTGCC GCGCTCTGGC      1560

CTGGAGGGAC AAGGCCAGCA CACGGTGCCT CAAC                                 1594
```

(2) INFORMATION FOR SEQ ID NO:2:

(i) SEQUENCE CHARACTERISTICS:
        (A) LENGTH: 423 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Leu Cys His Arg Gly Gly Gln Leu Ile Val Pro Ile Ile Pro Leu
 1               5                  10                  15

Cys Pro Glu His Ser Cys Arg Gly Arg Arg Leu Gln Asn Leu Leu Ser
            20                  25                  30

Gly Pro Trp Pro Lys Gln Pro Met Glu Leu His Asn Leu Ser Ser Pro
        35                  40                  45

Ser Pro Ser Leu Ser Ser Val Leu Pro Pro Ser Phe Ser Pro Ser
    50                  55                  60

Pro Ser Ser Ala Pro Ser Ala Phe Thr Thr Val Gly Gly Ser Ser Gly
65                  70                  75                  80

Gly Pro Cys His Pro Thr Ser Ser Leu Val Ser Ala Phe Leu Ala
                85                  90                  95

Pro Ile Leu Ala Leu Glu Phe Val Leu Gly Leu Val Gly Asn Ser Leu
            100                 105                 110

Ala Leu Phe Ile Phe Cys Ile His Thr Arg Pro Trp Thr Ser Asn Thr
        115                 120                 125

Val Phe Leu Val Ser Leu Val Ala Ala Asp Phe Leu Leu Ile Ser Asn
    130                 135                 140

Leu Pro Leu Arg Val Asp Tyr Tyr Leu Leu His Glu Thr Trp Arg Phe
145                 150                 155                 160

Gly Ala Ala Ala Cys Lys Val Asn Leu Phe Met Leu Ser Thr Asn Arg
                165                 170                 175

Thr Ala Ser Val Val Phe Leu Thr Ala Ile Ala Leu Asn Arg Tyr Leu
            180                 185                 190

Lys Val Val Gln Pro His His Val Leu Ser Arg Ala Ser Val Gly Ala
        195                 200                 205

Ala Ala Arg Val Ala Gly Gly Leu Trp Val Gly Ile Leu Leu Leu Asn
    210                 215                 220

Gly His Leu Leu Leu Ser Thr Phe Ser Gly Pro Ser Cys Leu Ser Tyr
225                 230                 235                 240

Arg Val Gly Thr Lys Pro Ser Ala Ser Leu Arg Trp His Gln Ala Leu
                245                 250                 255

Tyr Leu Leu Glu Phe Phe Leu Pro Leu Ala Leu Ile Leu Phe Ala Ile
            260                 265                 270

Val Ser Ile Gly Leu Thr Ile Arg Asn Arg Gly Leu Gly Gly Gln Ala
        275                 280                 285

Gly Pro Gln Arg Ala Met Arg Val Leu Ala Met Val Val Ala Val Tyr
    290                 295                 300

Thr Ile Cys Phe Leu Pro Ser Ile Ile Phe Gly Met Ala Ser Met Val
305                 310                 315                 320
```

```
Ala Phe Trp Leu Ser Ala Cys Arg Ser Leu Asp Leu Cys Thr Gln Leu
            325                 330                 335

Phe His Gly Ser Leu Ala Phe Thr Tyr Leu Asn Ser Val Leu Asp Pro
            340                 345                 350

Val Leu Tyr Cys Phe Ser Ser Pro Asn Phe Leu His Gln Ser Arg Ala
            355                 360                 365

Leu Leu Gly Leu Thr Arg Gly Arg Gln Gly Pro Val Ser Asp Glu Ser
            370                 375                 380

Ser Tyr Gln Pro Ser Arg Gln Trp Arg Tyr Arg Glu Ala Ser Arg Lys
385                 390                 395                 400

Ala Glu Ala Ile Gly Lys Leu Lys Val Gln Gly Glu Val Ser Leu Glu
                405                 410                 415

Lys Glu Gly Ser Ser Gln Gly
            420
```

(2) INFORMATION FOR SEQ ID NO:3:

(i) SEQUENCE CHARACTERISTICS:
        (A) LENGTH: 1435 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
GGCACGAGCT GCCTTCCTGG CACCAATCCT GGCCCTGGAG TTTGTCCTGG GCCTGGTGGG      60

GAACAGTTTG GCCCTCTTCA TCTTCTGCAT CCACACGCGG CCCTGGACCT CCAACACGGT     120

GTTCCTGGTC AGCCTGGTGG CCGCTGACTT CCTCCTGATC AGCAACCTGC CCCTCCGCGT     180

GGACTACTAC CTCCTCCATG AGACCTGGCG CTTTGGGGCT GCTGCCTGCA AAGTCAACCT     240

CTTCATGCTG TCNACCAACC GCAAGGCCAG CGTTGTCTTC CTCACAGCCA TCGCACTCAA     300

CCGCTACCTG AAGGTGGTGC ANCCCCACCA CGTGCTGAAC CGTGCTTCCG TGGGGGCANC     360

TGCCCGGGTG GNCGGGGGAA TCTGGGTGGG CATCCTGCTC CTCAACGGGN ACCTGCTCCT     420

GAACACCTTC TCCGGCCCCT CCTGCCTCAG CTACAGGGTG GGCACGAARC CCTCGGCCTC     480

GCTCCGCTGG CACCAGGCAC TGTACCTGCT GGARTTYTTC CTGCCACTGG CGCTCATCCT     540

CTTTGCTATT GTGAGCATTG GGCTCACCAT CCGGAACCGT GGTCTGGGCG GGCAGGCAGG     600

CCCGCAGAGG GCCATGCGTG TNCTGGCCAT GGTGGTGGCY GTCTACACCA TCTGCTTCTT     660

GCCCAGCATC ATCTTTGGCA TGGCTTCCAT GGTGGCTTTC TGGCTGTCCG CCTGCCGATC     720

CCTGGACCTC TGCACACAGC TCTTCCATGG CTCCCTGGCC TTCACCTACC TCAACAGTGT     780

CCTGGACCCC GTGCTCTACT GCTTCTCTAG CCCCAACTTC CTCCACCAGA ACCGGGCCTT     840

GCTGGGCCTC ACGCGGGGCC GGCAGGGCCC AGTGAGCGAC GAAAGCTCCT ACCAACCCTC     900

CAGGCAGTGG CGCTACCGGG AGGCCTCTAG GAAGGCGGAR GCCATAGGGA AGCTGAAAGT     960

GCAGGGCGAG GTCTCTCTGG AAAAGGAAGG CTCCTCCCAA GGGCTGAAGG CCAGCTGCAG    1020

GGCTGCAGCG CTGTGGGGGT AAGGGCTGCC GCGCTCTGGC CTGGARGGAC AAGGCCAGCA    1080

CACGGTGCCT CAACCAACTG GACAAGGGAT GGCGGCAGAC CARGGGCCAG GCCAAAGCAC    1140

TGGCAGGACT CAGGTGGGTG GCAGGKARAR AAACCCACCT TAGGCCTCTC AGTGTGTCCA    1200

GGATGGCATT CCCAGAATGC AGGGGAGAGC AGGATGCCGG GTGGAGGAGA CAGGCAAGGT    1260

GCCGTTGGCA CACCAGCTCA GACAGGGGCC TGCGCAGCTG CAGGGGACAG ACGCCCAATC    1320
```

```
ACTGTCACAG CAGAGTCACC TTAGAAATTG GACAGCTGCA TGTTCTGTGC TCTCCAGTTT      1380

GTCCCTTCCA ATATTAATAA ACTTCCCTTT TAAATATAAA AAAAAAAAAA AAAAA           1435
```

(2) INFORMATION FOR SEQ ID NO:4:

(i) SEQUENCE CHARACTERISTICS:
        (A) LENGTH: 476 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Ala Arg Ala Ala Phe Leu Ala Pro Ile Leu Ala Leu Glu Phe Val Leu
 1               5                  10                  15

Gly Leu Val Gly Asn Ser Leu Ala Leu Phe Ile Phe Cys Ile His Thr
            20                  25                  30

Arg Pro Trp Thr Ser Asn Thr Val Phe Leu Val Ser Leu Val Ala Ala
        35                  40                  45

Asp Phe Leu Leu Ile Ser Asn Leu Pro Leu Arg Val Asp Tyr Tyr Leu
    50                  55                  60

Leu His Glu Thr Trp Arg Phe Gly Ala Ala Cys Lys Val Asn Leu
65                  70                  75                  80

Phe Met Leu Ser Thr Asn Arg Lys Ala Ser Val Val Phe Leu Thr Ala
                85                  90                  95

Ile Ala Leu Asn Arg Tyr Leu Lys Val Val Xaa Pro His His Val Leu
                100                 105                 110

Asn Arg Ala Ser Val Gly Ala Xaa Ala Arg Val Xaa Gly Gly Ile Trp
            115                 120                 125

Val Gly Ile Leu Leu Leu Asn Gly Xaa Leu Leu Leu Asn Thr Phe Ser
130                 135                 140

Gly Pro Ser Cys Leu Ser Tyr Arg Val Gly Thr Lys Pro Ser Ala Ser
145                 150                 155                 160

Leu Arg Trp His Gln Ala Leu Tyr Leu Leu Glu Phe Phe Leu Pro Leu
                165                 170                 175

Ala Leu Ile Leu Phe Ala Ile Val Ser Ile Gly Leu Thr Ile Arg Asn
                180                 185                 190

Arg Gly Leu Gly Gly Gln Ala Gly Pro Gln Arg Ala Met Arg Val Leu
            195                 200                 205

Ala Met Val Val Ala Val Tyr Thr Ile Cys Phe Leu Pro Ser Ile Ile
    210                 215                 220

Phe Gly Met Ala Ser Met Val Ala Phe Trp Leu Ser Ala Cys Arg Ser
225                 230                 235                 240

Leu Asp Leu Cys Thr Gln Leu Phe His Gly Ser Leu Ala Phe Thr Tyr
                245                 250                 255

Leu Asn Ser Val Leu Asp Pro Val Leu Tyr Cys Phe Ser Ser Pro Asn
                260                 265                 270

Phe Leu His Gln Asn Arg Ala Leu Leu Gly Leu Thr Arg Gly Arg Gln
            275                 280                 285

Gly Pro Val Ser Asp Glu Ser Ser Tyr Gln Pro Ser Arg Gln Trp Arg
    290                 295                 300

Tyr Arg Glu Ala Ser Arg Lys Ala Glu Ala Ile Gly Lys Leu Lys Val
305                 310                 315                 320

Gln Gly Glu Val Ser Leu Glu Lys Glu Gly Ser Ser Gln Gly Leu Lys
                325                 330                 335
```

```
Ala Ser Cys Arg Ala Ala Ala Leu Trp Gly Gly Leu Pro Arg Ser Gly
            340             345             350

Leu Glu Gly Gln Gly Gln His Thr Val Pro Gln Pro Thr Gly Gln Gly
        355             360             365

Met Ala Ala Asp Gln Gly Pro Gly Gln Ser Thr Gly Arg Thr Gln Val
    370             375             380

Gly Gly Arg Xaa Xaa Asn Pro Pro Ala Ser Gln Cys Val Gln Asp Gly
385             390             395                         400

Ile Pro Arg Met Gln Gly Arg Ala Gly Cys Arg Val Glu Glu Thr Gly
            405             410             415

Lys Val Pro Leu Ala His Gln Leu Arg Gln Gly Pro Ala Gln Leu Gln
            420             425             430

Gly Thr Asp Ala Gln Ser Leu Ser Gln Gln Ser His Leu Arg Asn Trp
        435             440             445

Thr Ala Ala Cys Ser Val Leu Ser Ser Leu Ser Leu Pro Ile Leu Ile
    450             455             460

Asn Phe Pro Phe Lys Tyr Lys Lys Lys Lys Lys
465             470             475
```